United States Patent [19]

Saito

[11] Patent Number: 5,188,109

[45] Date of Patent: Feb. 23, 1993

[54] ARTIFICIAL DENTAL ROOT

[76] Inventor: Shigeru Saito, No. 8-17-40, Zushi-shi, Kanagawa-ken, Japan

[21] Appl. No.: 707,134

[22] Filed: May 30, 1991

[30] Foreign Application Priority Data

May 30, 1990 [JP] Japan ............................... 2-140785

[51] Int. Cl.⁵ ............................................. A61B 5/05
[52] U.S. Cl. .................................. 128/635; 128/903; 128/777
[58] Field of Search ............... 128/635, 631, 903, 777, 128/787, 419 F

[56] References Cited

U.S. PATENT DOCUMENTS

| | | | |
|---|---|---|---|
| 3,297,021 | 4/1964 | Davis et al. | 128/777 |
| 3,340,866 | 9/1967 | Nöller | 128/635 |
| 4,431,004 | 2/1984 | Besseman et al. | 128/635 |
| 4,844,076 | 7/1989 | Lesho et al. | 128/903 |
| 4,979,509 | 12/1990 | Hakky | 128/635 |

OTHER PUBLICATIONS

"Radio Pill Broadcasts From Stomach", Radio & TV News Jun. 1957, p. 114.
"An Accurate, Long-Term pH-Sensitive Radio Pill for Ingestion and Implantation", Colson et al., Biotelemetry Patient Monit. 8: No. 4/213-217, (1981).
"Power Sources for Implanted Telemetry Systems" T. Fryer, Biotelemetry 1/No. 1/31-40, (1974).

Primary Examiner—Lee S. Cohen
Assistant Examiner—Jeffrey P. Jastrzab
Attorney, Agent, or Firm—Jacobson, Price, Holman & Stern

[57] ABSTRACT

There is provided an aritifical dental root to be implanted into a jawbone comprising a sensor capable of contacting body fluids and a radio transmitter for transmitting electric signals representing the physical and/or chemical values of the body fluids obtained by the sensor to an external receiver. With such an artificial dental root, the blood, the lymph and the muscles of the carrier of the artificial dental root can be examined without pain on the side of the subject to continuously watch the health conditions of the subject regardless of the psychological well-being of the subject and the doctor watching the subject on a receiving set for the radio transmitter can intervene for the health of the subject, take measures to cure, if any, the disease of the subject and give directions for emergency treatment whenever necessary.

4 Claims, 1 Drawing Sheet

ARTIFICIAL DENTAL ROOT

BACKGROUND OF THE INVENTION

1. Field of the Invention

This invention relates to an artificial dental root to be advantageously used for detecting abnormal conditions, or diseases, in the inside of a human or other living body.

2. Prior Art

In recent years, health-consciousness is almost ubiquitously observed in families in advanced societies and a variety of instruments and devices for health examination are being widely used. However, with any of the existing instruments and devices, the subject has to be constrained during a health examination and therefore health information on the subject cannot be obtained on a continual basis and without pain as perceived by the subject.

In order to resolve this problem, there has been proposed a finger ring incorporating a sensor for collecting health information concerning the wearer and a radio transmitter for transmitting the information obtained by the sensor (Japanese Patent Publication: Tokkai Shou No. 57-11633). While such a sensor can procure information on blood pressure, body temperature and pulse on a constant basis, it cannot detect the blood sugar level of the wearer because it only touches the skin surface of the wearer.

There has been proposed an instrument of a combination of a heater and a sensor, whereby the subject is heated by the heater to accelerate perspiration, which is then medically analyzed by the sensor to provide health information on the subject (Japanese Patent Publication: Tokkai Shou No. 63-31638). However, such an instrument cannot be constantly carried by the subject nor can it provide information on blood, lymph and muscles. Therefore, if the blood of a subject has to be examined, an invasive instrument such as a syringe needle, a catheter or a sensor is required to be introduced into the body to collect a sample of blood for each examination. This type of procedure is incapable of collecting health information on a constant basis and is accompanied by loss of blood, psychological as well as physical pain on the side of the subject and the risk of infection.

A body terminal has been proposed (Japanese Patent Publication: Tokkai Shou No. 63-9435). It is a device in which one end is subcutaneously implanted in the body of the subject while the other end is projecting from the body so that the inside and the outside of the body are electrically connected by a conductor arranged in a through bore of the body terminal. A sensor is connected to the conductor at its internal end which an instrument is connected to its external end for diagnosis or medical treatment.

However, a body terminal as described above can become a nuisance for the subject if it remains subcutaneously within the body for a prolonged period of time with one of its end projecting from, for instance, the scalp. Moreover, it is easily imaginable that the subject can psychologically and physically suffer from the operation of burying the terminal in his or her body. Finally, the subject will be required to move often to a location where the instrument to be connected to the terminal is installed.

In view of the disadvantages of the prior art and the fact that artificial dental roots, bodies projecting from the gums of the carriers, are acquiring popularity in recent years, it is therefore an object of the present invention to provide an artificial dental root equipped in an appropriate manner with a sensor and a radio transmitter for transmitting electric signals representing the physical and chemical values obtained by the sensor so that the blood, the lymph and the muscles of the carrier of the artificial dental root can be examined without pain experienced by the subject to continuously watch the health conditions of the subject regardless of the psychological well-being of the subject and that the doctor watching the subject on a receiving set for the radio transmitter can control the health of the subject, take measures to cure, if any, the disease of the subject and give directions for emergency treatment whenever necessary.

Another object of the present invention is to provide an artificial dental root of the type as described above that additionally comprises a charging terminal for charging the battery to be used as power source for the transmitter so that the artificial dental root may serve for health examination for a very long period of time.

A third object of the present invention is to provide an artificial dental root of the type as described above by referring to the first object of the invention that additionally comprises a storage area for storing a battery to be used as power source for the transmitter so that the battery may be replaced whenever necessary and hence the artificial dental root may serve for health examination for a very long period of time.

A fourth object of the present invention is to provide an artificial dental root of the type as described above by referring to the first object of the invention that additionally comprises a lid for the transmitter or both the transmitter and the sensor so that either or both the transmitter and the sensor may be taken out by removing the lid for repair or replacement and hence the artificial dental root may serve for health examination semipermanently.

SUMMARY OF THE INVENTION

According to the invention, the first object of the invention is achieved by providing an artificial dental root incorporating a sensor capable of contacting body fluids and a radio transmitter for transmitting electric signals representing the physical and/or chemical values of the body fluids obtained by the sensor to an external receiver.

The second object of the invention is achieved by providing an artificial dental root similar to the one as described above that additionally comprises a charging terminal exposed at an upper section of the artificial dental root and connected to the battery to be used as power source for the transmitter.

The third object of the invention is achieved by providing an artificial dental root similar to the one as described above relative to the first object of the invention that additionally comprises a storage area for storing a battery to be used as power source for the transmitter, said storage area being capable of being closed for holding a battery in it and opened for access to the battery.

The fourth object of the invention is achieved by providing an artificial dental root similar to the one as described above relative to the first object of the invention that additionally comprises a lid for removably storing the transmitter or the transmitter and the sensor within the artificial dental root.

With an artificial dental root designed to achieve the first object of the invention, since its lower end is implanted in the jawbone of the subject in a known manner, the sensor is put in contact with body fluids such as blood and lymph and, if appropriately arranged, with part of the gums of the subject so that the sensor can obtain from the body fluids their physical and/or chemical values necessary for determining, for instance, the seriousness of diabetes, malignant tumors, liver cirrhosis or leukemia the carrier of the artificial dental root has, which are then sent and received in the form of electric signals.

Therefore, with a radio receiver for receiving the electric signals sent from the transmitter, the doctor in charge can constantly watch the subject for any abnormal conditions regardless of the location of the subject within the service area of the transmitter.

With an artificial dental root designed to achieve the second object of the invention, since the battery serving as power source for the transmitter can be recharged whenever necessary by way of the charging terminal partly exposed at an upper portion of the artificial dental root, the transmitter can continue its normal operation semipermanently.

With an artificial dental root designed to achieve the third object of the invention, since a storage area is provided for storing the battery for the transmitter that can be replaced and held there by an appropriate closing means, the transmitter can enjoy a prolonged service life.

With an artificial dental root designed to achieve the fourth object of the invention, since the lid can be removed from the artificial dental root to take out the transmitter or both the transmitter and the sensor, they can be repaired or replaced without difficulty.

Now, the present invention will be described in greater detail by referring to the accompanying drawings that illustrate preferred embodiments of the invention.

DETAILED DESCRIPTION OF THE INVENTION

Figure 1:
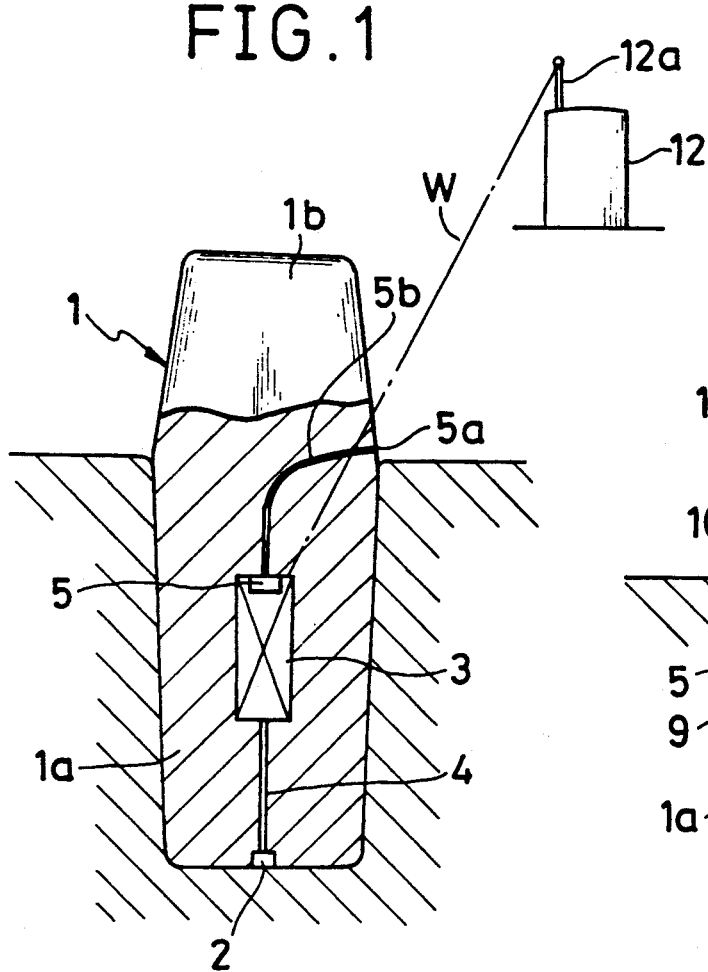
FIG. 1 is a sectional view of a preferred embodiment of the invention.

In FIG. 1 illustrating in longitudinal cross section an embodiment designed to achieve the first object of the invention, artificial dental root 1 that can be made of a material selected from a variety of known materials in an established manner comprises a sensor for detecting abnormal conditions or diseases within the body that carries it and a transmitter connected to the sensor. In FIG. 1, sensor 2 is located at the lower portion 1a of the artificial dental root 1 with its bottom exposed to the body and the lead wire 4 from the sensor 2 is connected to the input side of the transmitter 3.

The transmitter 3 is vertically aligned with the artificial dental root 1 and therefore located at the center of the latter. Reference numeral 5 in FIG. 1 denotes a battery, or power source, of the transmitter 3. A charging terminal 5a as described above relative to the second object of the invention is exposed to atmosphere at an upper portion 1b of the artificial dental root 1 so that the battery 5 may be recharged by way of the charging terminal 5a and the connector wire 5b arranged in the artificial dental root 1 whenever necessary.

It should be noted that teeth are the only hard components of a body that are exposed to atmosphere without coverings and an artificial dental root 1 is implanted in the dental root membrane, the jawbone and the gums from its lower portion 1a, while its upper portion 1b is exposed as it stands upright from the gums.

Figure 3:
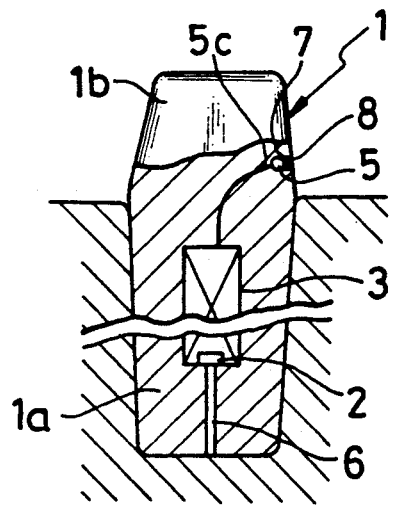
FIG. 3 is a sectional view of still another preferred embodiment of the invention.
Figure 4:
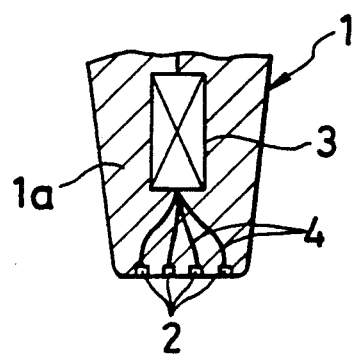
FIG. 4 is a sectional view of an embodiment of the invention comprising a plurality of sensors.

The sensor 2 may be appropriately arranged on or in the artificial dental root 1 in such a manner that it comes in contact with body fluids such as blood and lymph as the artificial dental root 1 is implanted. While the bottom of the sensor 2 is exposed on the lower end of the artificial dental root 1 in the embodiment of FIG. 1, the sensor 2 is located adjacent to the transmitter 3 at the upper end of a conduit 6 having an opening at the bottom of the artificial dental root 1 as shown in FIG. 3. In the embodiment of FIG. 4, a plurality of sensors 2, 2 . . . are arranged on the lower end of the artificial dental root 1 with their bottoms exposed to the tissue supporting the artificial dental root 1.

If the sensor 2 is a glucose sensor for continuously detecting the blood sugar level of a patient suffering from diabetes, the detected blood sugar level will be used to determine the seriousness of the diabetes of the patient so that he or she may be cared for on constant basis. The use of a film of fixed enzyme such as a film of glucose oxidase for the glucose sensor is an established technique.

Since cancer cells produce proteins and sugars which are specific to the type of cancer present, a sensor for detecting such proteins and sugars can be realized by applying a membrane of monoclonal antibodies to the surface of a sensor having platinum or silver electrodes to catch any electric currents produced by those materials of the cancer cells.

The transmitter 3 may be selected from a variety of candidate transmitters, although a transmitter of a type that intermittently operates is recommendable for minimization of noise and battery consumption and other considerations.

Now, an embodiment designed to achieve the third object of the invention will be described by referring to FIG. 3. In this embodiment, the power source 5 of the transmitter is removably stored in a storage area 7 having an opening and the power source 5 is connected to a power input terminal 5c of the transmitter 3.

The storage area 7 that contains the power source 5 is normally enclosed by a lid 8, which can be removed whenever necessary for replacement of the power source 5.

Figure 2:
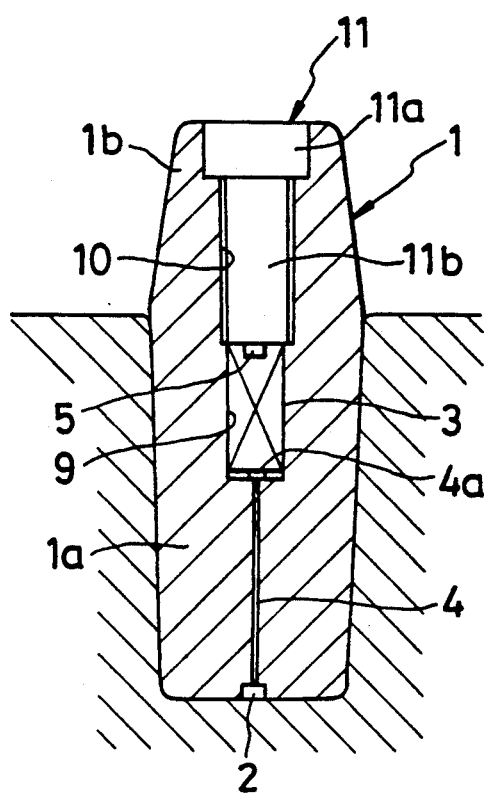
FIG. 2 is a sectional view of another preferred embodiment of the invention.

A fourth embodiment of the invention designed to achieve the fourth object of the invention will be described by referring to FIG. 2 of the accompanying drawings. This embodiment differs from the embodiment of FIG. 1 in that the storage chamber 9 for removably accommodating the transmitter 3 is located at the center of the artificial dental root 1 around its longitudinal axis and that an access space 10 is provided in the upper portion 1b of the artificial dental root 1 and above the storage chamber 9 in communication with the latter in order to allow an easy access to the storage chamber 9 from outside as its upper end is open to the outside, although the access space 10 is normally closed by a removable lid 11.

The lid 11 has a head section 11a and a threaded rod section 11b projecting from the head section 11a. Although the artificial dental root 1 may be so designed that both the transmitter 3 and the sensor 2 can be taken out by removing the lid 11, the embodiment of FIG. 2 is so arranged that only the transmitter can be taken out from the storage chamber 9 as terminal 4a connected to the lead wire 4 of the sensor Z is accommodated in the storage chamber 9 and the transmitter 3 stored in the storage chamber 9 is connected to the terminal 4a.

Thus, with an artificial dental root 1 as described above, since the sensor 2 is constantly kept in touch with body fluids, their physical and/or chemical values can be transmitter from the transmitter 3 in the form of electric signals on a carrier wave W, which are then received by a receiver 12 located at home or in a hospital and additionally illustrated in FIG. 1 by way of an antenna 12a so that they may be constantly observed by a person in charge regardless of the location of the patient within the effective area of the transmitter and without confining the patient.

With the embodiment of FIG. 1, the power source 5 can be recharged by way of a charging terminal 5a. With the embodiment of FIG. 3, the power source 5 stored in the storage area 7 can be replaced whenever necessary. With the embodiment of FIG. 2, both the transmitter 3 and the sensor 2 can be replaced by removing the removable lid 11.

As is apparent from the above description, since an artificial dental root designed to achieve the first object of the invention can be implanted in a living person when he or she wants such an artificial dental root for inevitable reasons, it does not give any additional pain to that person at the time of implantation. Moreover, once the artificial dental root is set in position, it does not cause any nuisance to the person as it becomes an indispensable part of his or her body and his or her daily activity is not restricted by it by any means, while its sensor is constantly detecting any abnormal conditions that have occurred within the body which are transmitted to the receiver in the form of electric signals so that information on the abnormal conditions or diseases of that person may reach the doctor or other person in charge with a high reliability and therefore any necessary measures may be taken quickly to medically protect the person.

An artificial dental root designed to achieve the second object of the invention is provided with a rechargeable battery. An artificial dental root designed to achieve the third object of the invention is provided with a replaceable battery. An artificial dental root designed to achieve the fourth object of the invention allows repair and replacement of the transmitter and/or sensors. Therefore these artificial dental roots can be used semipermanently.

What is claimed is:

1. An implant for transmitting body conditions of a living animal to an external receiver comprising an artificial dental root having a lower end adapted to be implanted in a jawbone of the animal and an exposed upper end, a sensor mounted in said root adapted to be in contact with body fluids of the animal, and radio transmitting means mounted in said artificial dental root connected with said sensor for transmitting body condition signals obtained by said sensor to an external receiver, said transmitting means including a means for transmitting signals representing physical values of the body fluid obtained by the sensor.

2. The implant as defined in claim 1 wherein said root includes a recharageable battery mounted in said root and connected to said transmitting means to form a power source for the transmitting means, and a charging terminal embedded in said root, said charging terminal being connected to said battery and exposed at an upper portion of said root.

3. An implant for transmitting body conditions of a living animal to an external receiver comprising an artificial dental root having a lower end adapted to be implanted in a jawbone of the animal and an exposed upper end, a sensor mounted in said root adapted to be in contact with body fluids of the animal, and radio transmitting means mounted in said artificial dental root connected with said sensor for transmitting body condition signals obtained by said sensor to an external receiver, said transmitting means including a means for transmitting signals representing chemical values of the body fluids obtained by the sensor.

4. The implant as defined in claim 3 wherein said root includes a rechargeable battery mounted in said root and connected to said transmitting means to form a power source for the transmitting means, and a charging terminal embedded in said root, said charging terminal being connected to said battery and exposed at an upper portion of said root.

* * * * *